United States Patent
Montgomery

(10) Patent No.: US 6,576,227 B1
(45) Date of Patent: *Jun. 10, 2003

(54) PEROXIDASE-ACTIVATING ORAL COMPOSITIONS

(75) Inventor: Robert E. Montgomery, Monterey, MA (US)

(73) Assignee: Oraceutical Innovative Properties, LLC, Lee, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/237,191

(22) Filed: Jan. 26, 1999

Related U.S. Application Data

(63) Continuation of application No. 08/698,474, filed on Aug. 15, 1996, now Pat. No. 5,908,614.
(60) Provisional application No. 60/012,537, filed on Feb. 29, 1996, and provisional application No. 60/002,361, filed on Aug. 15, 1995.

(51) Int. Cl.[7] ............ A61K 7/20; A61K 33/40; A61K 9/68; A61K 7/28; A61C 5/00
(52) U.S. Cl. ............ 424/50; 424/53; 424/613; 424/440; 424/490; 433/215.1
(58) Field of Search ............ 424/50, 53, 440, 424/490, 613; 433/215.1

(56) References Cited

U.S. PATENT DOCUMENTS

| | | | | |
|---|---|---|---|---|
| 4,150,113 A | * | 4/1979 | Hoogendoorn et al. | 424/50 |
| 4,178,362 A | * | 12/1979 | Hoogendoorn et al. | 424/50 |
| 4,269,822 A | * | 5/1981 | Pellico et al. | 424/50 |
| 4,421,669 A | * | 12/1983 | Brichard | 252/95 |
| 4,564,519 A | * | 1/1986 | Pellico et al. | 424/50 |
| 4,578,265 A | * | 3/1986 | Pellico et al. | 424/50 |
| 4,788,052 A | * | 11/1988 | Ng et al. | 424/53 |
| 4,839,156 A | * | 6/1989 | Ng et al. | 424/53 |
| 4,839,157 A | * | 6/1989 | Ng et al. | 424/53 |
| 4,891,211 A | * | 1/1990 | Winston | 424/53 |
| 4,988,500 A | * | 1/1991 | Hunter et al. | 424/53 |
| 5,043,176 A | * | 8/1991 | Bycroft et al. | 426/335 |
| 5,227,161 A | * | 7/1993 | Kessler | 424/94.4 |
| 5,250,299 A | * | 10/1993 | Good et al. | 424/94.4 |
| 5,258,132 A | * | 11/1993 | Kamel et al. | 252/94 |
| 5,264,205 A | * | 11/1993 | Kelly | 424/53 |
| 5,370,815 A | * | 12/1994 | Kessler | 252/106 |
| 5,374,368 A | * | 12/1994 | Hauschild | 252/95 |
| 5,496,542 A | * | 3/1996 | Hauschild | 424/53 |
| 5,505,875 A | * | 4/1996 | Beaujean et al. | 259/99 |
| 5,631,000 A | * | 5/1997 | Pellico et al. | 424/53 |
| 5,741,525 A | * | 4/1998 | Larsen | 424/613 |
| 5,888,505 A | * | 3/1999 | Allen | 424/94.4 |
| 5,908,614 A | * | 6/1999 | Montgomery | 424/53 |

* cited by examiner

Primary Examiner—Shep K. Rose
(74) Attorney, Agent, or Firm—Banner & Witcoff, Ltd.

(57) ABSTRACT

A peroxidase-activating oral care composition, in accordance with an embodiment of the invention, includes a non-enzymatic, water-soluble hydrogen peroxide precursor and a pH-adjusting agent capable of producing a selected pH in an aqueous solution. The composition facilitates the rapid release of hydrogen peroxide and results in the activation of a peroxidase enzyme in an oral cavity. A process for manufacturing the oral care composition including obtaining the precursor, dispersing it in a non-hygroscopic material so as to coat or encapsulate it, obtaining and associating the coated or encapsulated particles with a pH-adjusting agent, and formulating the particles into an oral care composition is provided in another embodiment. In addition, a method for activating a peroxidase system in an oral cavity of an animal, including selecting a non-enzymatic water soluble hydrogen peroxide precursor, mixing the precursor with a pH-adjusting agent, and administering the precursor and pH-adjusting agent in a suitable formulation to the oral cavity, is provided in a further embodiment of the invention.

11 Claims, No Drawings

PEROXIDASE-ACTIVATING ORAL COMPOSITIONS

RELATED U.S. APPLICATIONS

This application is a continuation of U.S. application Ser. No. 08/698,474, filed Aug. 15, 1996, now U.S. Pat. No. 5,908,614, for an invention by Montgomery, which claims priority from U.S. Provisional Application Serial No. 60/002,361, filed Aug. 15, 1995, and from U.S. Provisional Application Serial No. 60/012,537, filed Feb. 29, 1996. All of these applications are hereby incorporated herein by reference.

TECHNICAL FIELD

This present invention relates to a method for activating a peroxidase enzyme system in situ.

BACKGROUND ART

A number of naturally occurring antimicrobial systems rely upon the ability of certain oxidizing agents to disrupt metabolic processes of bacteria, fungi and viruses. Examples of such oxidizing agents include hypothiocyanite (OSCN—/HOSCN), hypochlorite (OCl—\HOCl), and hypoiodite (OI—\HOI). These agents are known to inhibit glycolysis, penetrate prokaryotic cell walls, and generally disrupt a wide variety of processes crucial to the survival of lower organisms at concentrations greater than or equal to about 100 micromoles per liter. The oxidizing agents are formed from the detoxification of hydrogen peroxide by mammalian peroxidase systems, such as those found in saliva, cervical fluid, lachrymal fluid, and leukocytes. Examples of such peroxidase system enzymes are myeloperoxidase, lactoperoxidase, and salivary peroxidase.

Attempts to exploit these natural antimicrobial systems have been directed to both the oral care field and the gastrointestinal tract. U.S. Pat. No. 4,150,113 and U.S. Pat. No. 4,178,362 (Hoogendorn, et al.) describe dentifrice compositions containing glucose oxidase that react with plaque and salivary glucose to produce low levels of hydrogen peroxide. Hydrogen peroxide production by such systems is, however, highly irregular due to the non-uniform distribution and unpredictable availability of substrate, namely glucose, in the oral cavity.

U.S. Pat. No. 4,269,822, U.S. Pat. No. 4,564,519 and U.S. Pat. No. 4,578,265 (Pellico, et al.) further describe dentifrice compositions containing an oxidoreductase enzyme and its specific substrate in an aqueous solution for the purpose of producing hydrogen peroxide or other antimicrobial oxidizing compounds such as hypothiocyanite ion. A more predictable amount of hydrogen peroxide (and subsequently hypothiocyanite ions) is produced by the compositions of Pellico et al., compared with those of the Hoogendorn references. The differences between the two compositions reflect the availability of glucose in the oral cavity as substrate for glucose oxidase.

There are, however, a number of disadvantages associated with the compositions of Pellico et al. These include: the limited rate of enzymatically-produced hydrogen peroxide that in turn produces the hypothiocyanite ion. The short duration of oral contact time, namely during toothbrushing, means that insufficient amounts of hypothiocyanite is available to effectively eliminate microbes in the oral cavity. In addition, the references utilize glucose oxidase as the oxidoreductase enzyme that in turn relies upon the availability of a sufficient concentration of glucose in solution to produce hydrogen peroxide. However, the glucose itself is a microbial substrate and is potentially cariogenic when present in an oral care product.

U.S. Pat. No. 4,564,519 describes a chewable dentifrice, such as a chewing gum or lozenge, which contains a dual enzyme system for producing hypothiocyanite ions upon being chewed or otherwise activated by the moisture in saliva. Such compositions suffer from similar drawbacks to those mentioned immediately above namely a slow rate of enzymatically-produced hydrogen peroxidase as well as a reliance on a cariogenic compound.

Other solid or chewable compositions capable of producing hydrogen peroxide or other oxidizing agents upon activation with moisture are taught in U.S. Pat. No. 4,320,116, U.S. Pat. No. 4,726,948, and U.S. Pat. No. 4,929,466. These compositions are foodstuffs intended for consumption by livestock in order to limit the growth of harmful bacterial within the animal's gastrointestinal tract. These references describe the use of various enzymatic and non-enzymatic sources for hydrogen peroxide, where the enzymatic sources are glucose oxidase/glucose and the non-enzymatic sources are sodium perborate, sodium percarbonate, and calcium peroxide. However, it is known that sodium percarbonate and potassium percarbonate have extremely alkaline pH and are thus of little use in activating the peroxidase enzymes until exposed to the acidic environment within the gastrointestinal tract. Thus, the foodstuff compositions described in the reference cannot be used as a therapeutic or otherwise peroxidase-activating effect in the oral cavity.

It would thus be advantageous to provide substantially non-cariogenic compositions capable of rapidly producing hydrogen peroxide in conditions that are suitable for peroxidase enzyme activation in the oral cavity.

It would also be advantageous to provide compositions capable of rapidly producing antimicrobial hypohalite ions within the limited contact time available in most oral hygiene procedures.

It would also be advantageous to provide compositions capable of rapidly producing antimicrobial hypohalite ions upon contact with saliva within the limited contact time available in most oral hygiene procedures.

SUMMARY

This invention satisfies the above needs. A novel oral care composition is provided.

A preferred embodiment of the invention is a non-enzymatic, water-soluble hydrogen peroxide precursor, capable of rapidly releasing an effective amount of hydrogen peroxide for activating the peroxidase system in the oral cavity, upon contact with an aqueous solution; and a pH adjusting agent capable of producing a selected pH in the aqueous solution for facilitating the rapid release of the hydrogen peroxide from the hydrogen peroxide precursor and the activation of the peroxidase enzyme in the oral cavity.

In a further embodiment of the invention, a process is provided for manufacturing an oral care product, comprising the steps of obtaining an alkali metal percarbonate; dispersing the percarbonate in a non-hygroscopic material so as to encapsulate the percarbonate; obtaining particles of percarbonate encapsulated in the non-hygroscopic material; associating the percarbonate particles with a pH adjusting agent; and formulating the particles into an oral care product.

In a further embodiment of the invention, a method is provided for activating a peroxidase system in an oral cavity of an animal, including the steps of selecting a non-enzymatic water soluble hydrogen peroxide precursor capable of rapidly releasing an effective amount of hydrogen peroxide for activating the peroxidase system in the oral cavity upon contact with an aqueous solution; mixing the precursor with a pH adjusting agent capable of producing a selected pH in the aqueous solution for facilitating the rapid release of the hydrogen peroxide from the hydrogen peroxide precursor and the activation of the peroxidase enzyme in the oral cavity; and administering to the oral cavity the precursor and pH-adjusting agent in a suitable formulation.

DETAILED DESCRIPTION OF THE INVENTION

The present invention relates to oral care compositions which upon contact with an aqueous solution, are capable of rapidly activating a peroxidase enzyme so as to release hydrogen peroxide.

The concentrations of the components of the oral composition are given in molar units which denote the concentration of the component in the aqueous contact solution.

The limiting factor in all of the mammalian antimicrobial peroxidase systems is the availability of the substrate, namely hydrogen peroxide. Furthermore, the pH of the aqueous environment determines not only the effective release of hydrogen peroxide from the precursor but also the activity of the peroxidase system and the efficacy of the resulting oxidizing agents in penetrating the cell walls of microorganisms.

It is known, for example, that the non-ionized species of hypohalite ions more readily penetrates the cell walls of microorganisms then does the ionized species thereby having increased efficiency in inhibiting the metabolism of the microorganisms. The distribution of ionized versus non-ionized species (for instance HOCl, or hypochlorous acid, versus OCl—, or hypochlorite ion) is highly pH dependent.

The pH activity profiles of the peroxidase enzymes lactoperoxidase, salivary peroxidase, and myeloperoxidase is maximum between pH 5 and 6, but drop off sharply below pH 4.0 and above pH 7.5. Thus, in order to maintain peroxidatic function, it is here concluded that the pH of the medium surrounding the peroxidase enzymes must be within the range of about pH 4.0 to about pH 7.5. This pH range also favors the anti-microbial, non-ionized hypohalite species which prevail at lower pH levels.

Consequently, the compositions of the invention include a non-enzymatic water-soluble hydrogen peroxide precursor and a water-soluble pH adjusting component capable of providing a pH to an aqueous contact solution of between about 4.0 and 7.9. The aqueous contact solution may commonly be saliva, but may also include an aqueous solution that is mixed with the precursor and pH adjusting agent prior to contact with the oral cavity.

The non-enzymatic water-soluble precursor may be selected from the group of stable persalts including, but not limited to, alkali metal percarbonates, for example, sodium and potassium percarbonate, alkali metal perborates, alkali metal peroxides, and hydrogen peroxide complexes such as carbamide peroxide. Preferred non-enzymatic hydrogen peroxide precursors are sodium percarbonate and carbamide peroxide due to their solubility characteristics and relatively benign toxicity in limited concentrations. The most preferred non-enzymatic hydrogen peroxide precursor is sodium percarbonate.

Sodium percarbonate is a relatively stable complex containing 2 moles of sodium carbonate complexed with 3 moles of hydrogen peroxide (27% hydrogen peroxide by weight). It is highly water soluble (120 grams per liter at 20° C.) and produces a pH upon dissolution of between 10 and 11 (for a 1% solution). Thus, although sodium percarbonate possesses the desirable hydrogen peroxide-releasing properties for the practice of the present invention, alone they are of little utility for the activation of a peroxidase enzyme due to their high in-solution pH properties. Accordingly, a pH adjusting agent has been utilized to normalize the pH to a range of 4.0–7.9.

Carbamide peroxide is a 1 to 1 molar complex between urea and hydrogen peroxide (35% hydrogen peroxide by weight) with a molecular weight of 94.07. It is usually manufactured in the form of crystals which are highly soluble in water (800 grams per liter of water at 20° C. to yield a saturated solution of 44.4% carbamide peroxide, equivalent to a hydrogen peroxide concentration of 15.5%). However, when carbamide peroxide is solubilized in water, a pH of approximately 3.40 (for a saturated solution) to approximately 4.05 (for a 1% solution) is obtained. This pH is slightly below the desirable range, according to the invention, for activating a peroxidase enzyme in the aqueous contact solution absent a pH adjusting agent.

The pH adjusting agent of the present invention may include any toxicologically acceptable and preferably water-soluble ingredient which is capable of producing an aqueous contact solution pH of between about 4.0 and about 7.5. Most preferably, the pH adjusting agent will provide a pH of between 5.0 and 6.0. Such pH adjusting agents include a wide variety of common buffers, acidulants, and/or alkalizers which are well known to those skilled in the art. Examples include organic acids and their alkali metal salts, such as citric acid, malic acid, butyric acid, gluconic acid, adipic acid, glutaric acid, and malonic acid; amines such as triethanolamine and tris(hydroxyaminomethane); alkali metal hydroxides, such as sodium hydroxide, potassium hydroxide, and ammonium hydroxide; and combinations thereof. Preferably, these pH adjusting agents are free of water of hydration in order to achieve long-term stability in the presence of the hydrogen peroxide precursor. The optimum concentration of the pH-adjusting agent is the lowest level necessary to achieve the desired pH adjustment of the aqueous contact solution to between 4.0 and 7.5. This concentration of the pH adjusting agent is in the range of about 0.01% by weight of the composition to about 1% by weight of the composition. However, higher and lower amounts may have utility in circumstances where the buffering capacity of the surrounding medium is either very strong or very weak, respectively.

The oral care composition described above generates hydrogen peroxide to be used as substrate for the peroxidase system in a manner that permits the concentration of hydrogen peroxide generated overall to be reduced while increasing the rate of its production. This provides a safe and effective antimicrobial composition. While the prior art describes antimicrobial activity associated with oral care products containing or generating hydrogen peroxide, the present invention provides for the first time the particular advantages of both limiting the concentration of hydrogen peroxide to a level which is suitable for the activation of a peroxidase enzyme (less than about 10 millimoles per liter in situ) and providing or limiting the pH range of the in situ composition/saliva fluids to that which is also most advantageous for activation of a peroxidase enzyme.

The antimicrobial activity of the oral compositions depend on the presence of an oxygen acceptor. The preferred oxygen acceptor for oral care applications (i.e., in the presence of salivary peroxidase or lactoperoxidase) is the thiocyanate ion, which can be provided to the composition through the inclusion of non-toxic levels of a thiocyanate salt, such as potassium or sodium thiocyanate. In general, the level of thiocyanate salt included in said compositions will be from about 1.0 millimolar to about 10.0 millimolar (again, as above, based upon the concentration achieved in the aqueous contact solution). However, the composition of the invention may be further enhanced by incorporating halide ions in the aqueous contact solution. One or more oxygen-accepting halide or pseudohalide ions, including any of chloride, iodide, bromide, and thiocyanate and combinations thereof, may be incorporated in the aqueous contact solution. These ions may already be present in solution (such as thiocyanate ion, which is present in saliva), or alternatively they may be provided as auxiliary components in the inventive compositions.

In general, oral care product use results in a dilution, of composition components on the order of 1 part composition to from about 1 part aqueous contact solution to about 5 parts aqueous contact solution (from about 1 to 1 to about 1 to 5). It is desirable that the non-enzymatic hydrogen peroxide precursors should be present at a level sufficient to release a minimum amount of hydrogen peroxide of approximately 100 micromoles per liter. A preferred range of hydrogen peroxide released is in the range of from about 500 micromoles per liter to about 2,000 micromoles per liter. The determination of the amounts of hydrogen peroxide that are released from a given composition in vitro (for instance, under controlled conditions in contact with distilled water as a diluent) are relatively simple to predict. However, the determination of amounts of hydrogen peroxide released in vivo indicates that in vivo levels are well below those predicted in vitro. This difference may result from the destruction of hydrogen peroxide by salivary catalase, interaction of hydrogen peroxide with various organic matter and non-enzymatic reducing agents in saliva, and the destructive effect of dissolved metal ions in saliva. Thus, while an upper limit of 2.0 millimoles of hydrogen peroxide per liter is predictive of an in vitro effectiveness, concentrations as high as 30 millimoles per liter may be desirable to produce much lower observed in vivo concentrations of hydrogen peroxide.

It should also be noted that an accumulation of high concentrations of hydrogen peroxide (greater than about 0.1 percent or about 29 millimoles per liter) ate not desirable due to the evidence that hydrogen peroxide is mutagenic and can cause cellular DNA damage at elevated concentrations. The prior art describes broad concentration ranges of hydrogen peroxide as halving utility in oral hygiene and tooth whitening applications, but makes little reference to the potential harmful effects of hydrogen peroxide at concentrations, for instance, in the range of 1.5 to 3.0 percent by weight (441 to 882 millimolar).

Although the peroxidase enzyme may typically be present in the aqueous contact solution (such as salivary peroxidase, which is resent in saliva), additional peroxidase enzyme, preferably lactoperoxidase, may be included in the inventive compositions in a range of from about 10 ABTS (2,2'-Azinobis(3-ethylbenzthiazoline sulfonic acid) units per gram of composition to about 1,000 ABTS units per gram of composition [under the assay conditions described in Pruitt, et al., Analytical Biochemistry 191, pp. 278–286 (1990)].

In a preferred embodiment of the invention, compositions may be non-aqueous, dry, or otherwise substantially water-free mixtures, which can be applied or deposited on or within an orally acceptable carrier, such as a chewing gum, dental floss, anhydrous dentifrice, or animal chew. These compositions, once dissolved in the aqueous solution at a selected pH, are capable of producing, in the absence of additional enzyme preparations, hydrogen peroxide that results in the rapid activation of an antimicrobial peroxidase enzyme system in vivo.

The hydrogen peroxide precursors of the invention, such as the alkali metal percarbonates, may be processed with little or no loss of activity from moisture pick-up if, prior to being deposited onto or into an orally acceptable carrier, the alkali metal percarbonate is first dispersed in a non-hygroscopic fluid or solid in order to coat or encapsulate each particle of the percarbonate prior to being entered into a manufacturing process. Alkali metal percarbonates processed in this manner show very little degradation during processing cycles due to moisture absorption and/or temperature exposure. Although the concept of coating moisture-sensitive materials with water-insoluble or non-hygroscopic outer layers is not new to the art, the inventive aspect of the present invention stems from the requirement that said coating must necessarily consist of a moisture-resistant fluid which has mobility and will form a fluid interface in contact with bulk moisture. Only through the formation of a thin interfacial layer in contact with bulk moisture will the intimately admixed alkali metal percarbonate and non-hygroscopic fluid release the alkali metal percarbonate (as hydrogen peroxide and an alkali metal carbonate) into the neighboring aqueous phase.

Preferred non-hygroscopic fluids and solids are non-solvents for alkali metal percarbonates. These fluids are water-insoluble, yet low enough in viscosity to be readily dispersed into a thin film or interface in the presence of bulk moisture. Such non-hygroscopic liquids include, but are not limited to, mineral oils, vegetable oils, fatty esters, silicone fluids, fluorinated hydrocarbons, and fluorosilicones. Preferred non-hygroscopic solids are also water insoluble and must be capable of being melt processed at a temperature suitable for maintaining the stability of the alkali metal percarbonate. Suitable non-hygroscopic solids include, but are not limited to, waxy solids such as mineral oils, vegetable oils, fatty esters, silicone fluids, fluorinated hydrocarbons, fluorosilicones, stearic acid, glyceryl monostearate, paraffin wax, microcrystalline wax, and fatty alcohols. An example of an applicable melt process includes batch melt processing, whereby the non-hygroscopic solid carrier is simply melted in bulk, whereupon the alkali metal percarbonate is added and dispersed. Another example of an applicable melt process is the fluid-bed processing technique described in U.S. Pat. No. 4,421,669, whereby the alkali metal percarbonate (in the form of a powdered or granular particle) is floated on an airstream and subsequently sprayed with melted droplets of the non-hygroscopic solid carrier.

Both non-hygroscopic fluid and solid carriers may also include the pH-adjusting agents of the present invention, so as to simplify the application of both inventive components (i.e., the hydrogen peroxide precursor and the pH-adjusting agent) onto or into the oral care product delivery system. Alternatively, the hydrogen peroxide precursor and the pH-adjusting agent may be dispersed separately within two different non-hygroscopic carriers and subsequently applied onto or into the oral care product delivery system in a stepwise fashion.

The choice of non-hygroscopic fluid or solid carrier for the alkali metal percarbonate is dependent upon the final oral care product delivery system contemplated. Where the formulation is an animal chew, such as a rawhide animal chew, the percarbonate may be dispersed in a non-hygroscopic fluid carrier before being deposited on the surface of the chew. Where the formulation is a chewing gum, the alkali metal percarbonate may be dispersed in either a non-hygroscopic liquid or solid, to be subsequently added batchwise to the gum base and thence kneaded to achieve homogeneity. Alternatively, the finished chewing gum may be coated with a layer of either a liquid or solid dispersion of alkali metal percarbonate.

The following examples serve to illustrate a number of the inventive compositions, but are by no means intended to limit the scope of the overall invention.

EXAMPLES

Example I

Production of Hypothiocyanite Ions in a pH Range of 3–9

The components of 8 compositions were added to a laboratory powder blender and mixed for 1 hour in order to assure complete mixing. The resulting white powders were extremely fine and free flowing.

Each sample 1A–1H (100 mg) was contacted with 100 ml distilled water at 25° C. and the resulting hydrogen peroxide concentration after 15 seconds [recorded as $H_2O_2$ (t=15 sec)] was determined by the method of Mottola, et al., Analytical Chemistry 42, pp. 410–411 (1970). The pH at 25° C. of each solution [recorded as pH (t=15 sec)] at the 15 second point was also determined. The results are recorded in Table 2 below.

TABLE 1

A comparison of 8 compositions (wt in gms)

| Component | A | B | C | D | E | F | G | H |
|---|---|---|---|---|---|---|---|---|
| Mannitol (Powder, USP) | 90 | 87 | 86 | 85.5 | 85 | 80 | 70 | 60 |
| Sodium Percarbonate Powder | 10 | 10 | 10 | 10 | 10 | 10 | 10 | 10 |
| Citric Acid (Powder, USP) | — | 3 | 4 | 4.5 | 5 | 10 | 20 | 30 |
| Total | 100 | 100 | 100 | 100 | 100 | 100 | 100 | 100 |

Fresh, whole unstimulated human saliva was collected from 3 subjects drooling into chilled plastic cups, said cups being placed in ice during and after the expectoration procedure, and the 3 samples of saliva pooled. A sample of the freshly-pooled saliva was warmed to 37° C. and evaluated for its hypothiocyanite ion concentration [recorded as OSCN (initial)] by the method of Mansson-Rahemtulla, et al., Archives of Oral Biology 31, 10, pp. 661–668 (1986). Readings recorded as AOSCN@ are intended to reflect the combined concentration of OSCN-ion and the non-ionized HOSCN species. The powdered compositions of the present example were then contacted with the pooled saliva at a concentration of 1.0 mg of powder in 1.0 ml of saliva. After 15 seconds, the saliva was reevaluated for its hypothiocyanite ion concentration as above [recorded as OSCN (t=15 sec)] and the results recorded in Table 2 below.

TABLE 2 hypothicyanite concentrations in saliva

| SAMPLE | 1A | 1B | 1C | 1D | 1E | 1F | 1G |
|---|---|---|---|---|---|---|---|
| $H_2O_2$ (t = 15 sec) in micromoles/liter | 750 | 765 | 760 | 755 | 760 | 760 | 765 |
| pH (t = 15 sec) @ 37 degrees C. | 9.17 | 7.95 | 7.20 | 6.10 | 4.89 | 3.82 | 3.10 |

TABLE 2-continued hypothicyanite concentrations in saliva

| SAMPLE | 1A | 1B | 1C | 1D | 1E | 1F | 1G |
|---|---|---|---|---|---|---|---|
| OSCN (initial) in micromoles/liter | 42 | 42 | 42 | 42 | 42 | 42 | 42 |
| OSCN (t = 15 sec) in micromoles/liter | 19 | 114 | 160 | 269 | 257 | 199 | 58 |

It can been seen from the above that the powdered compositions of Table 1 which result in a solution pH of from about 3.82 to 7.95 are capable of rapidly elevating the concentration of hypothiocyanite ions in pooled, unstimulated whole human saliva. Supplementation of the maninitol in Table 1 with potassium thiocyanate (at a level capable of providing a 1.0 millimolar concentration of thiocyanate ion in the pooled saliva sample) resulted in an even more dramatic increase in the observed hypothiocyanite ion concentration, probably due to the reaction-limiting concentration of naturally occurring thiocyanate in the pooled saliva sample.

Example II

A Comparison of Hydrogen Peroxide Concentrations Produced in Vivo and in Vitro

The composition of Sample 1D was combined, in different proportions, with pooled saliva in order to produce pH-adjusted saliva containing varying concentrations of hydrogen peroxide [recorded as $H_2O_2$ (actual)]. The theoretical concentration of hydrogen peroxide is also shown [recorded as $H_2O_2$ (theoretical)]. The concentrations of OSCN produced are also recorded in Table 3 below. All measurements were made at t=15 seconds after mixing the prescribed weight of Sample 1D with saliva.

grams of distilled water for 15 seconds. At exactly the 15 second point, a sample of the resulting fluid was assayed for hydrogen peroxide and pH as in Example I. The fluid contained a hydrogen peroxide concentration of 360 micromolar and the fluid pH was 6.03.

Saliva samples from five subjects, ages 25–45, were collected as above, but rather than being pooled, were assayed individually for hypothiocyanite ion concentrations. The results are recorded below. The same volunteers were then asked to chew the coated chewing gum samples for a period of 2 minutes. Their saliva was collected again, and their salivary hypothiocyanite ion levels recorded. (Table 4). The results show a remarkable ability of the inventive composition to impart salivary peroxidase-activating properties to the chewing gum.

TABLE 4

| SUBJECT | OSCN BEFORE | OSCN AFTER |
|---|---|---|
| 1 | 29 micromolar | 214 micromolar |
| 2 | 56 micromolar | 198 micromolar |
| 3 | 45 micromolar | 260 micromolar |
| 4 | 39 micromolar | 252 micromolar |
| 5 | 28 micromolar | 208 micromolar |

TABLE 3

| EXAMPLE ID (MG/LITER) | $H_2O_2$ (theoretical) (MICROMOLES/ LITER) | $H_2O_2$ (actual) (MICROMOLES/ LITER) | pH | OSCN (MICROMOLES/ LITER) NO ADDED SCN- | OSCN (MICROMOLES/ LITERS) SCN-@ 1 MILLIMOLAR |
|---|---|---|---|---|---|
| 10 | 7.94 | <1 | 5.86 | 38 | 42 |
| 100 | 79.4 | <1 | 6.02 | 88 | 87 |
| 1,000 | 794 | 52 | 6.10 | 285 | 420 |
| 2,000 | 1,588 | 120 | 6.18 | 321 | 598 |
| 4,000 | 3,176 | 2,185 | 6.20 | 339 | 712 |
| 6,000 | 4,764 | 3,890 | 6.25 | 301 | 690 |
| 10,000 | 7,941 | 6,920 | 6.25 | 233 | 662 |
| 20,000 | 15,882 | 13,202 | 6.26 | 110 | 272 |
| 40,000 | 31,764 | 29,990 | 6.25 | 93 | 160 |
| 100,000 | 79,410 | 78,540 | 6.25 | 37 | 90 |

Example III

Hypothiocyanite Ion Concentrations Resulting From an Oral Composition on Chewing Gum The composition of sample 1D was applied to the surface of 3.0 gram sticks of chewing gum at a coating rate of 0.05% by weight of gum in order to produce chewing gum which was capable of generating hydrogen peroxide upon contact with saliva, in addition to providing for a salivary pH adjustment to about 6.0.

One stick of Sample 1D-coated chewing gum (3.05 grams) was broken into small pieces and vortexed with 3.05

Example IV

Hydrogen Peroxide Concentrations Resulting From an Oral Composition on a Rawhide Chew A rawhide animal chew was prepared by taking 10 pounds of dried, unbasted rawhide chews, approximately 2 inches wide by 6 inches in length, and spray coating them at a 1.0 percent coating rate with the following composition;

TABLE 5

| COMPONENT | AMOUNT |
| --- | --- |
| Light Mineral Oil USP | 87 grams |
| Sodium Percarbonate (Solvay-FB100) | 10 grams |
| Malic Acid (Powder FCC) | 3 grams |
| TOTAL | 100 grams |

The above components were slurried until a fine dispersion of solids was obtained. Agitation continued during the spray process to prevent the settling out of the solids. The sprayed rawhide chews were dried at room temperature for 24 hours, during which time the initial surface gloss observed on the freshly sprayed chews disappeared.

In order to determine the ability of the spray-coated rawhide chew to generate pH-adjusted hydrogen peroxide upon contact with water, single chews cut into four pieces and weighed. An equivalent amount of distilled water was weighed out and the coated chews vortexed in the water for 15 seconds. The Achew fluid@ contained a hydrogen peroxide concentration of 6.53 millimolar at a pH of 5.84 at 25° C.

Example V

Delivery of the Oral Composition in a Gel

An anhydrous carbamide peroxide gel composition was prepared in order to demonstrate another option for delivery of the composition to the oral cavity.

TABLE 6

| COMPONENT | AMOUNT |
| --- | --- |
| Glycerine 99.7% USP | 93.45 grams |
| Carbopol 980 NF (BF Goodrich) | 2.00 grams |
| Carbamide Peroxide (Degussa) USP | 0.05 grams |
| Distilled Water | 3.00 grams |
| Tris(hydroxymethyl)aminomethane USP | 1.50 grams |
| TOTAL | 100 grams |

The Carbopol 980 NF was dispersed under high shear in the Glycerine 99.7% USP and subsequently deaerated. The Carbamide Peroxide was then dissolved in this mixture under low shear mixing. The Tris(hydroxymethyl) aminomethane was dissolved in the Distilled Water, and this phase dispersed into the main phase under 28@ Hg vacuum in order to avoid entrapment of air. The resulting gel was highly viscous and transparent.

In the above composition, the tris(hydroxymethyl) aminomethane USP serves as both a neutralizer for thickening the acidic carboxypolymethylene (Carbopol 980 NF) and as an alkalizer to provide a suitable peroxidase-active pH during the use of this product. The pH of a 1:5 dilution (1 part Example V to 5 parts Distilled Water) is 5.4, and the dilution showed a hydrogen peroxide concentration of 969 micromoles per liter.

I claim:

1. An oral care composition for activating a peroxidase system in an animal oral cavity, comprising:
   a non-aqueous or otherwise substantially water-free dentifrice;
   a non-enzymatic, water-soluble, finely divided hydrogen peroxide precursor material incorporated within the dentifrice, the material capable of rapidly releasing an effective amount of hydrogen peroxide for activating the peroxidase system in the oral cavity upon contact with an aqueous solution, the material coated or encapsulated by being dispersed in a water insoluble, non-hygroscopic, viscous fluid or in a film-forming, melt-processable waxy solid, the fluid or solid selected from the group consisting of:
   (a) liquid mineral oils, vegetable oils, fatty esters, silicone fluids, fluorinated hydrocarbons and fluorosilicones, or (b) solid mineral oils, vegetable oils, fatty esters, silicone fluids, fluorinated hydrocarbons, fluorosilicones, stearic acid, glycerin monosterate, paraffin wax, microcrystalline wax, and fatty alcohols the fluid or solid being a non-solvent of the material; and
   a pH-adjusting agent capable of producing a selected pH of between about 4.0 and about 6.5 in the aqueous solution.

2. A composition according to claim 1, wherein the material is finely divided sodium percarbonate.

3. A composition according to claim 1, wherein the material is finely divided carbamide peroxide.

4. A composition according to claim 1, wherein the material is finely divided calcium peroxide.

5. A composition according to claim 1, further comprising:
   an abrasive.

6. A composition according to claim 1, further comprising:
   a flavorant.

7. A composition according to claim 1, further comprising:
   a thickener.

8. A composition according to claim 1, further comprising:
   an alkali metal thiocyanate.

9. A composition according to claim 8, further comprising:
   a peroxidase enzyme.

10. A process for manufacturing an oral care composition, comprising:
    obtaining non-enzymatic, water-soluble, finely divided hydrogen peroxide precursor material,
    providing a non-aqueous or otherwise substantially water-free dentifrice,
    dispersing the finely divided hydrogen peroxide precursor material in a water insoluble, non-hygroscopic, viscous fluid or in a film-forming, melt-processable waxy solid, the fluid or solid selected from the group consisting of:
    (a) liquid mineral oils, vegetable oils, fatty esters, silicone fluids, fluorinated hydrocarbons and fluorosilicones, or (b) solid mineral oils, vegetable oils, fatty esters, silicone fluids, fluorinated hydrocarbons, fluorosilicones, stearic acid, glycerin monosterate, paraffin wax, microcrystalline wax, and fatty alcohols, the fluid or solid being a non-solvent of the finely divided hydrogen peroxide precursor material, so as to coat or encapsulate the finely divided hydrogen peroxide precursor material,
    associating the finely divided hydrogen peroxide precursor material with a pH-adjusting agent capable of producing a selected pH of between about 4.0 and about 6.5 in an aqueous solution, and incorporating the associated material within the dentifrice.

11. A method of activating a peroxidase system in an oral cavity of an animal, comprising:

selecting non-enzymatic, water-soluble, finely divided hydrogen peroxide precursor material capable of rapidly releasing an effective amount of hydrogen peroxide for activating the peroxidase system in the oral cavity upon contact with an aqueous solution, the material coated or encapsulated by being dispersed in a water insoluble, non-hygroscopic, viscous fluid or in a film-forming, melt-processable waxy solid, the fluid or solid selected from the group consisting of:

(a) liquid mineral oils, vegetable oils, fatty esters, silicone fluids, fluorinated hydrocarbons and fluorosilicones, or (b) solid mineral oils, vegetable oils, fatty esters, silicone fluids, fluorinated hydrocarbons, fluorosilicones, stearic acid, glycerin monosterate, paraffin wax, microcrystalline wax, and fatty alcohols, the fluid or solid being a non-solvent of the material, mixing the material with a pH-adjusting agent capable of producing a selected pH of between about 4.0 and about 6.5 in the aqueous solution, and administering to the oral cavity, the material and pH-adjusting agent incorporated within a non-aqueous or otherwise substantially water-free dentifrice.

* * * * *